United States Patent [19]

Berick

[11] 4,267,451

[45] May 12, 1981

[54] RADIOACTIVITY DETECTION IN HIGH-PRESSURE LIQUID CHROMATOGRAPHY

[75] Inventor: Alan C. Berick, Concord, Calif.

[73] Assignee: Varian Associates, Inc., Palo Alto, Calif.

[21] Appl. No.: 965,766

[22] Filed: Dec. 4, 1978

[51] Int. Cl.³ ............................ G01T 1/00; G01T 1/20
[52] U.S. Cl. ...................................... 250/328; 250/367
[58] Field of Search ................... 250/328, 361 R, 366, 250/367; 73/61.1 C

[56] References Cited

U.S. PATENT DOCUMENTS

| | | | |
|---|---|---|---|
| 3,898,460 | 8/1975 | Noakes et al. | 250/328 |
| 4,019,372 | 4/1977 | Parkell et al. | 73/61.1 C |

Primary Examiner—Alfred E. Smith
Assistant Examiner—Janice A. Howell
Attorney, Agent, or Firm—Stanley Z. Cole; Norman E. Reitz

[57] ABSTRACT

In a high-pressure liquid chromatography system, a radioactive sample in the effluent from a chromatographic column can be detected by passing the effluent into a cell packed with a fluorescent composition comprising a scintillation material chemically bonded to an inert substrate. A suitable fluorescent composition is microparticulate didansyl-N-2-aminoethyl-3-aminopropyl silica. Radioactive emissions from the sample cause scintillations in the fluorescent composition that can be detected through the walls of the cell. In order to obtain a chromatogram of the radioactivity occurring in the column, aliquots of the effluent from the column may be passed sequentially into a plurality of cells arranged on a carousel support structure that is rotable in stepwise fashion so that each cell passes in turn through a fill station, a detection station, and a wash station. At the fill station, each cell in turn is filled with an aliquot of effluent. As one cell is being filled at the fill station, the scintillations occurring in another cell are being monitored at the detection station, while still another cell is being washed at the wash station in order to remove the aliquot of effluent previously monitored for radioactivity. After being washed, each cell can subsequently be filled with a fresh aliquot of effluent at the fill station.

5 Claims, 3 Drawing Figures

RADIOACTIVITY DETECTION IN HIGH-PRESSURE LIQUID CHROMATOGRAPHY

BACKGROUND OF THE INVENTION

This invention is a further development in the detection of radioactive species by high-pressure liquid chromatography.

In particular, this invention relates to the detection of radioactive species in the effluent from a chromatographic column by passing the effluent through a cell packed with a material that is caused to fluoresce by radioactive emissions in the cell.

More particularly, the present invention provides an apparatus and method for obtaining a chromatogram in real time for the radioactivity occurring in a chromatographic column.

Various techniques have been used in the prior art to detect a radioactive species in the effluent from a chromatographic column by monitoring scintillations produced in a fluorescent composition by radioactive emissions from the species to be detected. According to one technique, the effluent from a chromatographic column was mixed with a "scintillation cocktail", and this mixture was then passed through an open tube (i.e., an unpacked flow cell). The "scintillation cocktail" comprised a fluorescent substance such as 2,5-diphenyl oxazole (known as PPO), which was caused to scintillate by the transfer of molecular excitation energy to it from a solvent such as toluene or dioxane that has been excited when bombarded by radioactive emissions. This "scintillation cocktail" technique is discussed in greater detail in *The Current status of Liquid Scintillation Counting*, edited by E. O. Branson, published by Grune & Stratton, 1970.

A disadvantage of the "scintillation cocktail" technique is that when the column effluent is aqueous, the ratio of the "scintillation cocktail" volume to the effluent volume must typically be in the range from 5:1 to 10:1 in order to counteract the quenching effect of the aqueous solvent upon the scintillation process, and in order to prevent aqueous precipitation of the scintillation material. Furthermore, to accommodate the addition of such a large quantity of "scintillation cocktail" to the effluent, the flow rate of the mixture through the open flow cell downstream of the column must be increased in order to permit the desired flow rate of the effluent through the column. Such an increase in the flow rate through the open flow cell tends to cause laminar flow-band broadening and reduced resolution.

Another disadvantage of the "scintillation cocktail" technique arises from the fact that a pump must be used to deliver the "scintillation cocktail" to the column effluent, thereby complicating and increasing the cost of the apparatus necessary for the monitoring of scintillations in the downstream flow cell. Furthermore, the "scintillation cocktail" material itself is costly; and the mixing of such a large volume of "scintillation cocktail" per unit volume of effluent is not economically feasible in many applications.

The concept of passing the effluent from a chromatographic column through a flow cell packed with a material that scintillates when exposed to radioactive emissions is also known to the prior art. A review of the pertinent prior art in this regard can be found in the specification of co-pending U.S. patent application Ser. No. 953,380, filed on Oct. 23, 1978, assigned to Varian Associates, Inc. A particular fluorescent composition that is suitable as a flow-cell packing for the monitoring of scintillations caused by radioactive emissions from a species in the effluent passing through a flow cell is microparticulate didansyl-N-2-aminoethyl-3-aminopropyl silica, which is claimed in U.S. patent application Ser. No. 953,380.

SUMMARY OF THE INVENTION

It is a general object of the present invention to provide an apparatus and method for obtaining a chromatogram of the radioactivity occurring in a chromatographic column.

It is a particular object of the present invention to provide apparatus and method for providing a chromatogram in real time for the radioactivity occurring in a chromatographic column.

In accordance with the present invention, successive aliquots of the effluent from a chromatographic column are passed in turn into each of a plurality of cells packed with a fluorescent composition that scintillates when bombarded by radioactive emissions from a species in the effluent introduced into the cell. A suitable fluorescent composition is a scintillation material chemically bonded to an inert substrate. A particular fluorescent composition for the practice of the present invention is microparticulate didansyl-N-2-aminoethyl-3-aminopropyl silica. The scintillations occurring in each one of the cells are monitored in turn by a scintillation counter to produce a real-time chromatogram of the radioactivity occurring in the chromatographic column.

An apparatus suitable for the practice of the present invention comprises a carousel support structure upon which a plurality of packed cells is arranged. The carousel is programmed to rotate in a stepwise fashion so that each cell passes in turn through a fill station, a detection station, and a wash station. At the fill station, the cells are filled in turn with successive aliquots of the effluent from the chromatographic column. During the time interval in which one cell is being filled, another cell on the carousel is positioned at the detection station at which scintillations occurring in that cell are counted. During that same interval of time, another cell that has already passed through the detection station is being washed at the wash station. The washing process involves removal of the aliquot of effluent that was previously measured for radioactivity at the detection station, and a further flashing of that cell by an appropriate solvent in order to remove substantially all traces of that aliquot.

In applications where the addition of a "scintillation solvent" to the effluent from the column is desirable in order to enhance the number of scintillations occurring as a result of radioactivity in the effluent, a "scintillation solvent" dispenser can be programmed to introduce an appropriate volume of "scintillation solvent" to each cell. The "scintillation solvent" can be added either at the wash station after the washing process has been completed, or at a separate dispenser station through which the washed cell passes prior to arriving at the fill station again.

Appropriate time intervals for each cell to remain at the various stations are predetermined according to the nature of the radioactive species to be detected; and the stepwire rotation of the carousel to provide such appropriate time intervals can be programmed according to techniques well known to those skilled in the art. Variations in the design of a chromatographic system utilizing the present invention are possible, and would be apparent to one skilled in the art upon a perusal of the following description of the preferred embodiment in conjunction with the accompanying drawing. Hence, the chromatographic system described hereinafter is illustrative rather than definitive of the invention.

DESCRIPTION OF THE PREFERRED EMBODIMENT

Figure 1:
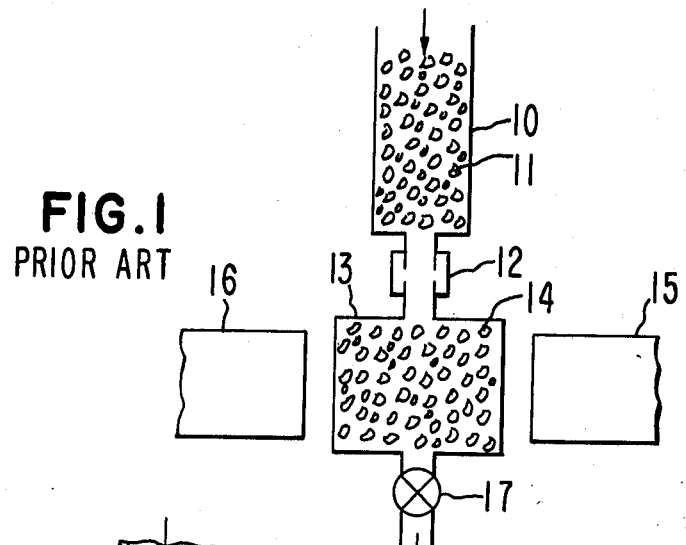
FIG. 1 is a schematic cross-sectional view of a chromatographic column coupled to a flow cell packed with a fluorescent composition that scintillates when exposed to radioactive emissions from a species in the effluent from the column.

FIG. 1 is representative of a prior art technique for detecting the presence of a radioactive species in the effluent from a chromatographic column 10. The column 10 is packed with a particulate material 11 that is termed a "stationary phase", which selectively adsorbs particular species dissolved in, or otherwise carried by, a solvent that is pumped through the column 10. In this way, the constituents of the solvent passing through the column 10 can be quantitatively analyzed on the basis of properties such as particle size, chemical composition and chemical affinity, by techniques well known to those skilled in the art of liquid chromatography.

In the system shown in FIG. 1, the chromatographic column 10 is coupled by a means of a swaged connector 12, such as a low dead-volume union, to a flow cell 13. The flow cell 13 is packed in accordance with the disclosure in co-pending U.S. patent application Ser. No. 953,380, with a fluorescent composition 14 that scintillates upon exposure to radioactive emissions from a species in the effluent from the column 10. Scintillations produced in the fluorescent composition 14 are detected through transparent walls of the flow cell 13 by a suitable scintillation counting means such as photomultiplier tubes 15 and 16 arranged as coincidence counters to monitor only those scintillations produced by radioactive emissions from radioactive species passing through the cell 13. Spurious events that might be caused by photomultiplier noise are thereby unrecorded.

Materials that scintillate upon exposure to radioactive emissions were well known in the prior art. It was known to apply certain kinds of scintillation materials as coatings on particulate substrates, and to pass the effluent from a chromatographic column through a flow cell packed with such coated particles. Scintillations occurring in such a packed flow cell could be measured by suitable means such as photomultiplier tubes, and the measurements so made provided a quantitative indication of the radioactivity occurring in the effluent. A problem encountered in the prior art, however, was that many solvents (e.g., toluene and dioxane) would wash the coated scintillation material away from the substrate particles, thereby requiring frequent recharging of the flow cell with freshly coated particles.

In co-pending U.S. patent application Ser. No. 953,380, a fluorescent composition is disclosed that is particularly useful as the flow-cell packing for the detection of radioactive species according to the present invention. Accordingly, the fluorescent composition described in that patent application, which is microparticulate didansyl-N-2-aminoethyl-3-aminopropyl silica, is the preferred packing composition for the practice of the present invention. It is desirable that the particles 14 be microparticulate (i.e., that the longest dimension of each particle be in the range from 5 to 10 microns) in order that low energy beta particles can reach the solid scintillation material from anywhere in the interstitial spaces between particles. Other suitable packing compositions for the practice of this invention include microparticulate silica, alumina, a cross-linked dextron, or a cross-linked polystyrene-divinylbenzene resin, to which a scintillation material is chemically bonded by a linking agent.

A valve 17 can be provided to retain effluent from the column 10 within the flow cell 13 for appropriate periods of time in order to enable a statistically accurate sampling to be obtained for the scintillations occurring in the cell 13 during successive time intervals. After each successive scintillation measuring interval, the valve 17 is opened for removal of the aliquot of effluent that has already been measured for radioactivity, after which the valve 17 is closed to allow a new aliquot to enter the cell 13 for the next scintillation measuring interval. In this way, a chromatogram of the radioactivity occurring in the cell 13 can be obtained. Typically, a time interval of 50 to 200 seconds is used to provide an indication of the extent of radioactivity in the flow cell 13 for each interval of time. After the chromatogram is obtained, the aliquot of effluent in the cell 13' can be released to a waste recepticle.

Figure 2:
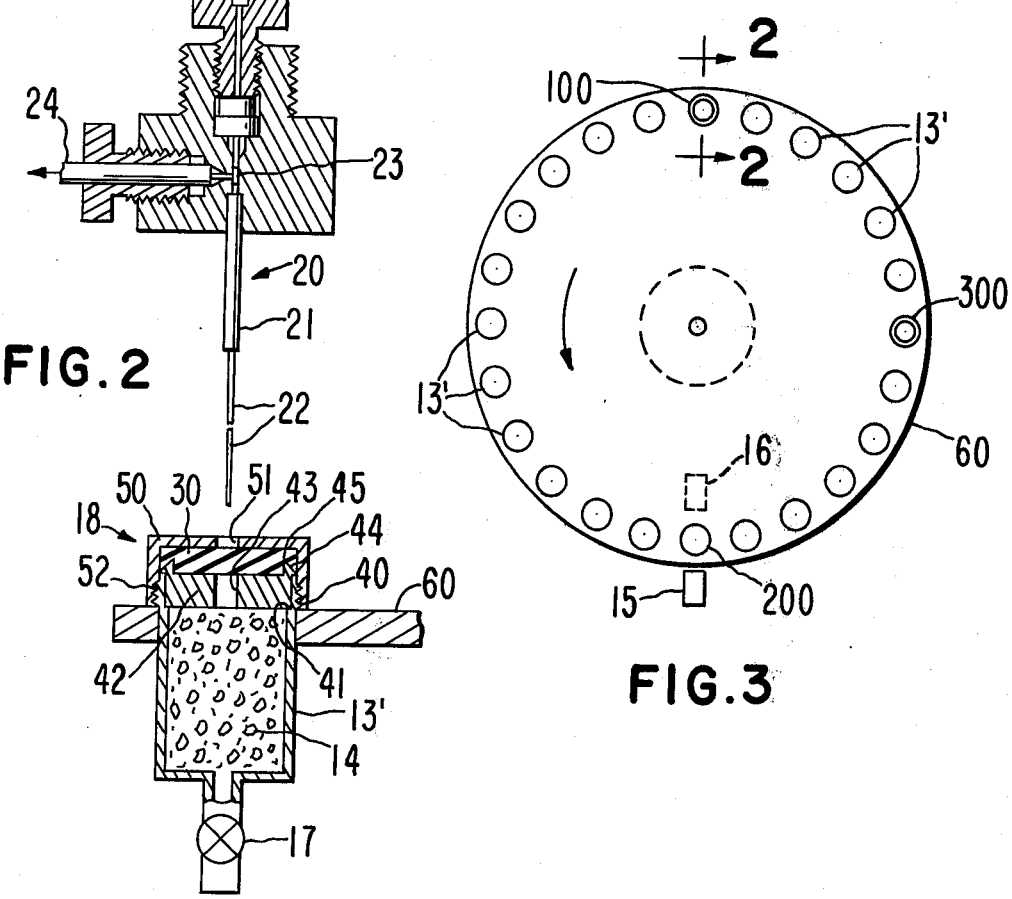
FIG. 2 is a schematic cross-sectional view along line 2—2 of FIG. 3 of a chromatographic column terminating in a needle structure through which aliquots of effluent can be introduced sequentially into a plurality of packed cells for the detection of radioactive species.

In accordance with the present invention, an on-line real-time chromatogram of the radioactivity occurring in the effluent passing through the chromatographic column 10 can be provided. As shown in FIG. 2, a needle structure 20 is attached at the end of the chromatographic column 10. The bore of the needle structure 20 is selected to provide a flow rate of from 0.5 to 4.0 milliliters per minute. Effluent is introduced by the needle structure 20 into the cell 13', which corresponds to the flow cell 13' shown in FIG. 1. However, the cell 13' of FIG. 2 might more appropriately be characterized as a static cell rather than as a flow cell because, as will be described in greater detail hereinafter in connection with FIG. 3, the technique of the present invention requires that each one of a plurality of similar cells be sequentially filled with effluent from the column 10, and that the radioactivity occurring in these individual cells be separately measured in sequence.

The cell 13' is a cylindrical glass vial that is fabricated so as to be able to couple at its bottom end, as by threading, with a valve 17 through which the cell 13' can be emptied and flushed. The valve 17, which may be of the type sold by Automatic Switch Company under the brand name ASCO "Red Hat", remains closed so as to retain an aliquot of effluent within the cell 13' while the cell is being filled and is opened to remove the aliquot and to enable washing of the cell 13' after the radioactivity of that aliquot has been measured.

The sealing structure 18 comprises an elastomeric septum 30 and an apertured cap structure 50, which holds the septum 30 in place. In operation, the needle structure 20 is aligned with an aperture 51 in the cap structure 50; and the septum 30 is then punctured in order to introduce an aliquot of effluent into the cell 13'.

The elastomeric septum 30 may be fitted over the cell 13' by a compression sealing device based upon that disclosed in U.S. Pat. No. 4,084,718 assigned to Varian Associates, Inc. According to this embodiment, the glass cell 13' is of generally cylindrical configuration, with screw threads 40 disposed on its outer surface near the upper end thereof, and with an annular ledge 41 on its inner surface near the upper end of the cell 13'. A metal plate 42 having a central aperture 43 is disposed on the ledge 41, with the aperture 43 being aligned with the aperture 51 in the cap structure 51. The plate 42 has an annular projection 44 extending vertically upward around its periphery. The projection 44 is configured to have an inner wall substantially perpendicular to the axis of the cylindrical cell 13', and an outer wall that tapers inwardly to intersect the perpendicular inner wall so as to form a sharp circular edge 45. The elastomeric septum 30 fits over the plate 42; and the cap structure 50 having screw threads 52 on its inner surface covers the plate 42 so as to sandwich the elastomeric septum 30 therebetween. The screw threads 52 on the inner surface of the cap structure 50 engage the screw threads 40 on the exterior surface of the cell 13' in order to secure the cap structure 50 to the cell 13'. Tightening of the cap structure 50 by screwing it onto the threaded portion 40 of the cell 13' causes the sharp edge 45 at the top of the plate 42 to cut into the elastomeric septum 30. In this way, the outer rim portion of the septum 30 is compressed between the tapered outer wall of the projection 44 and the inner wall of the cap structure 50, thereby providing a fluid-tight seal in the manner of a compressed O-ring between the cell 13' and the cap structure 50. The central portion of the septum 30 is left relatively stress-free, and is therefore able to withstand repeated puncturing by the needle structure 20.

The volume of sample material needed to provide an adequate analysis of the radioactivity present therein is about 1.0 milliliters. A cell 13' suitable for this purpose would typically be a cylindrical configuration having an inside diameter of 0.23 inch and a height of 3 inches. At a typical flow rate in the range from 0.5 to 4.0 milliliters per minute through the column 10, approximately 25 seconds would be required to fill the cell 13' to approximately 90% of its height. A time interval of approximately 25 seconds for counting the scintillations emitted from the fluorescent composition 14 packing the cell 13' having the above dimensions would usually be sufficient to provide a statistically adequate indication of the level of radioactive emissions from a species in the effluent. Consequently, an on-line chromatogram in real time of the radioactivity occurring in a cell having the above dimensions is possible. In certain applications, the volume of the cell 13' should be approximately two times larger than the volume of the aliquot of effluent introduced therein, for reasons explained hereinafter in connection with the capability of adding a scintillation solvent.

Figure 3:
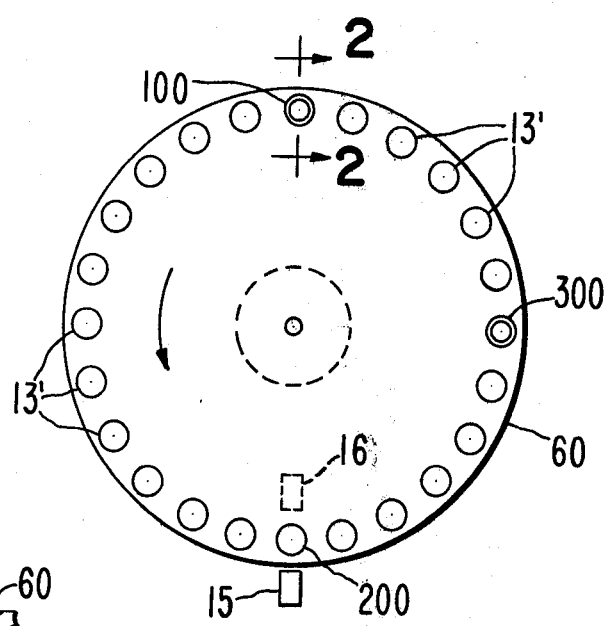
FIG. 3 is a schematic representation in plan view of a carousel support structure upon which a plurality of packed cells of the type shown in FIG. 2 can be arranged for sequential passage through a fill station, a detection station and wash station in accordance with the method of the present invention.

The static cell 13' as shown in FIG. 2 is representative of a plurality of similar cells mounted around the perimeter of a rotatable carousel-type support structure 60, as shown schematically in FIG. 3. The carousel 60 is rotatable in a stepwise fashion so as to provide an interval of approximately 25 seconds in each stopped state, with about one second being required to rotate the carousel 60 between sequential stopped states. At any given stopped state, one particular cell is located at a fill station 100 at which effluent from the column 10 can enter the cell through the membrane 30 by means of the needle structure 20. During that same given stopped state, another cell is located at a detection station 200 at which the scintillations occurring during the time interval of that stopped state are detected by the photomultiplier tubes 15 and 16. During that same time interval, yet another cell is located at a wash station 300 at which the cell is emptied of the aliquot that was previously monitored at the detection station 200 during an earlier stopped state. At the wash station 300, the cell can further be flushed to remove substantially all traces of the aliquot that has already been measured for radioactivity.

A mechanism for causing the needle structure 20 to align itself with the aperture 51 in the cap structure 50, and to move vertically when so aligned so as to puncture the septum 30 of whatever cell happens to be at the fill station 100, can be provided by any suitable technique known to those skilled in the art. Very high precision is not required for this alignment because the septum 30 is much larger than the diameter of the injection needle.

Referring to FIG. 3, twenty-four cells 13', each having an outside diameter of approximately 0.25 inch, are located around the periphery of the circular carousel support structure 60. The diameter of the carousel 60 is approximately 12 inches.

The carousel support structure 60 can be caused to rotate in stepwise fashion by a stepping motor technique using rotary solenoids. The present invention provides a real-time, on-line chromatogram of the radioactivity occurring in the chromatographic column 10. Accordingly, each cell 13' is filled substantially immediately after the previous cell in the sequence around the periphery of the carousel 60 is filled. The time interval of only 1.0 second between the shift of one cell away from the fill station 100 and the arrival of the next cell at that station causes effluent to drip from the needle structure onto the carousel 60 at a rate of only about 40 microliters per shift. This "loss" is tolerable in most circumstances.

A refinement in sophistication of an instrument according to this invention would use a valve arrangement to allow the needle structure 20 to release effluent only when each cell 13' is at the fill station 100.

Pressure pulses in the chromatographic column 10 can be avoided by using a device such as that shown in FIG. 2 for the needle structure 20. With this device, the column 10 has a constant flow therethrough, with effluent going to a fluid collector except when being delivered into cell 13'. As shown in FIG. 2, the needle structure 20 comprises an outer tube 21 and an inner needle 22. The outer tube 21 passes effluent from the column 10 when a valve 23 is open (i.e., in the "up" position), which occurs when the needle 22 is depressed—as when the needle 22 is in contact with the bottom of the inside of one of the cells 13'. In this open position of the valve 23, effluent can pass into the cell 13' via the tube 21 and the needle 22. When the needle 22 is raised up from contact with the bottom of a cell 13' (i.e., between fill intervals for adjacent cells), the valve 23 is caused to close (i.e., to move to the "down" position). Thus, when there is no bottom of a cell to depress the needle 22, the needle 22 falls so that the valve 23 blocks the entry to effluent into the tube 21, but instead directs the effluent into a tube 24 leading to the collector (not shown). In this way, the effluent flows at a steady rate through the column 10 without dripping onto the carousel 60. In this way, the sequential analysis at the detection station 200 of each of the cells that has previously passed through the fill station 100 can provide a time-varying chromatogram of the radioactivity occuring in the column 10.

At the wash station 300, a solvent can be introduced into each cell in sequence by means of a technique similar to that used for the introduction of effluent at the fill station 100 via the needle structure 20. The washing solvent serves to flush out from each cell the aliquot of effluent that was monitored for radioactivity at the detection station 200. The solenoid actuated valve 17 on each of the cells 13' is opened at the wash station 300, whereby the washing can occur.

In particular applications where it is desirable to add a scintillation solvent to each cell in order to increase the number of scintillations occurring therein, means may be provided, either at the wash station 300 or at a separate station (not shown in FIG. 3) located between the wash station 300 and the fill station 100, at which the scintillation solvent can be added to each cell. Typical scintillation solvents are toluene, dioxane and p-xylene. If a scintillation solvent is to be added at the wash station 300, the solenoid-actuated valve 17 would be closed before the scintillation solvent is added. As mentioned above, the volume of each cell may be larger than the volume of the aliquot of liquid added at the fill station 100 in order to accommodate the subsequent addition of scintillation solvent.

On-line analysis of radioactivity in the effluent from a chromatographic column was not performed in the past because of the low sensitivity of prior art detection techniques. It was customary in the prior art to use vials of 10 to 15 cubic centimeter capacity in order to permit the addition of sufficient "scintillation cocktail" to enhance the detectability of the scintillations. With the technique of the present invention, the individual cells 13' need only have a capacity of 1 to 2 cubic centimeters because the bonded scintillation material used as the cell packing 14 is less subject to quenching than the "scintillation cocktail" required in the prior art. The parallel execution of the fill, detection and wash steps according to the present invention permits on-line analysis of the radioactivity occuring in the column effluent.

To obtain a real-time chromatogram of radioactivity in the prior art, it would have been necessary to use a large volume of costly "scintillation cocktail" (e.g., a mixture of solvent and scintillation phosphors), which was not reusable. According to the present invention, nothing is needed in most cases to enhance the detectability of the scintillations occurring in the bonded scintillation material. In particular cases where it is desirable to enhance the detectability of the scintillations, a relatively small amount (e.g., on the order of one milliliter) of an inexpensive scintillation solvent is all that has to be added.

This invention has been set forth in terms of a particular embodiment. Clearly, other techniques are possible for delivering effluent to the packed cells 13', and other configurations can be visualized for positioning the individual cells 13' in sequence for reception of aliquots of the effluent. Furthermore, the chromatographic column whose effluent is to be analyzed could be a capillary column or a micro-column as well as a standard packed column as indicated in FIG. 2. Such variations in technique and configuration would be within the scope and spirit of the present invention, and consequently the embodiment shown herein is to be considered as illustrative and not limiting. The invention is limited only by the following claims and their legal equivalents.

What is claimed is:

1. An apparatus for producing an on-line, real-time chromatogram of the concentrations of radioactive peaks present in a liquid sample separated on a liquid chromatographic column by using a scintillation material bonded to an inert substrate, comprising:
   a carousel mechanism having a plurality of sample cells arranged thereon on a circumferential track thereof, said sample cells being packed with said scintillation material;
   fluoresence detection means positioned adjacent said circumferential track so that as said carousel rotates, each of said sample cells is brought adjacent said detection means in stepwise fashion for detection of fluoresence produced by radiation in the portion of said sample in said cell;
   means for filling said sample cells with said portion of said sample separated on said chromatographic column, said filling means being positioned adjacent said circumferential track upstream of said detection means; and
   means for flushing said portion of said sample from said sample cells, said flushing means being positioned adjacent said circumferential track downstream of said detection means.

2. An apparatus in accordance with claim 1 wherein said sample cell comprises at its uppermost end an apertured cap and elastomeric septum for receiving a syringe through which said portion of said sample is injected and wherein said sample cell contains a valve at its bottom end to permit said flushing means to operate.

3. An apparatus in accordance with claim 2 wherein said detection means comprises a pair of photomultiplier tubes positioned on opposing sides of said circumferential track to accomplish coincidence detection of said radiation produced fluorescence.

4. An apparatus in accordance with claim 3 in combination with solvent injection means to introduce a solvent to said sample for enhancement of scintillation detection.

5. An apparatus in accordance with claim 4 wherein said solvent injection means is incorporated in said filling means.

* * * * *